Figure 1:
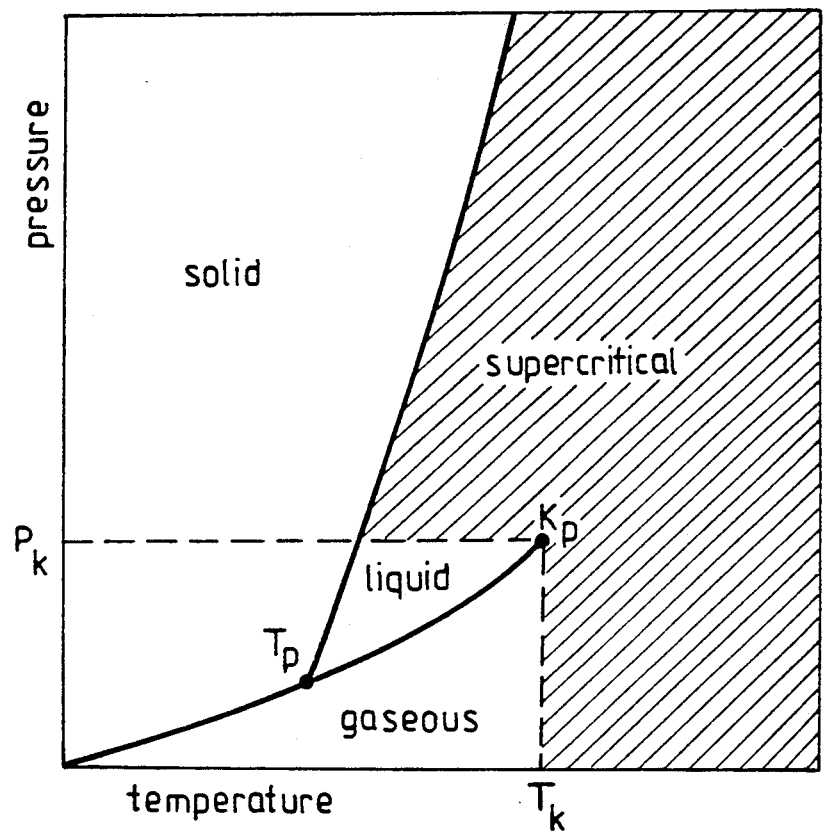

United States Patent [19]

Peter et al.

[11] Patent Number: 5,110,509
[45] Date of Patent: May 5, 1992

[54] PROCESS FOR THE RECOVERY OF MONOGLYCERIDES AND DIGLYCERIDES FROM A MIXTURE CONTAINING MONOGLYCERIDES, DIGLYCERIDES, AND TRIGLYCERIDES

[75] Inventors: Siegfried K. Peter, Lindenweg 3, Uttenreuth, Fed. Rep. of Germany, D-8525; Eckhard O. Weidner, Erlangen, Fed. Rep. of Germany; Ulrich M. Ender, Erlangen, Fed. Rep. of Germany; Bernd A. Czech, Erlangen, Fed. Rep. of Germany

[73] Assignee: Peter K. Siegfried, Uttenreuth-Weiher, Fed. Rep. of Germany

[21] Appl. No.: 385,313

[22] Filed: Jul. 24, 1989

[30] Foreign Application Priority Data

Jul. 25, 1988 [DE] Fed. Rep. of Germany ....... 3825248

[51] Int. Cl.⁵ .............................................. C11C 3/02
[52] U.S. Cl. ................................... 554/184; 554/189; 554/210
[58] Field of Search ........................................ 260/410.7

[56] References Cited

U.S. PATENT DOCUMENTS 4,466,923 8/1989 Friedrich ..................... 260/410.7

*Primary Examiner*—Paul J. Killos
*Attorney, Agent, or Firm*—Horst M. Kasper

[57] ABSTRACT

Described is a process for the recovery of monoglycerides and diglycerides from a mixture containing monoglycerides, diglycerides and triglycerides by extraction with a supercritical extractant which comprises specific cosolvents. After the separation of the monoglycerides as bottom product in the separation column, the extract consisting of diglycerides and triglycerides is separated into diglycerides and triglycerides by fractionated pressure decrease and change of temperature in two consecutive regeneration columns. A portion of the product obtained in the first regeneration column is fed as reflux to the head of the separation column, and a portion of the product, obtained in the second regeneration column, is fed as reflux to the head of the first regeneration column for an improved separation.

23 Claims, 2 Drawing Sheets

PROCESS FOR THE RECOVERY OF MONOGLYCERIDES AND DIGLYCERIDES FROM A MIXTURE CONTAINING MONOGLYCERIDES, DIGLYCERIDES, AND TRIGLYCERIDES

BACKGROUND OF THE INVENTION

1. Field of the Invention

The invention relates to a process for the recovery of monoglycerides and diglycerides from a mixture containing monoglycerides, diglycerides, and triglycerides by extraction in countercurrent with a supercritical extractant.

2. Brief Description of the Background of the Invention Including Prior Art

Monoglycerides are partial esters of glycerol with higher molecular fatty acids. Commercially available monoglycerides consist of mixtures of monoesters and diesters with minor additions of triesters, and they may be obtained by transesterification of triglycerides with glycerol or by reaction of glycerol with fatty acids.

Monoglycerides possess emulsifying, stabilizing, plasticizing and thickening properties. As the monoesters and diesters of glycerol are edible, they are used in various fields of the foodstuff industry, pharmaceutical industry, and in cosmetics. Normally, monoglycerides are water/oil emulsifiers, but by minor additions of, for example soaps, polyethylene oxide compounds, sulfated alcohols, they become "self-emulsifying" and are good oil/water emulsifiers under these conditions. Depending on the additive, they are able to form acid-stable and electrolyte-stable emulsions. The monoglycerides of higher fatty acids, such as, for example, glycerol monostearate, are used as lubricants in the processing of plastic materials. Monoglycerides obtained by molecular distillation and having a monoglyceride content of more than 90% are mainly used in the foodstuff industry, such as in farinaceous products, sweets and baking additives, margarine, ice cream.

By the addition of monoglyceride, up to 5% of palmitic acid/stearic acid-monoglycerides with a purity of 90% or of 10% palmitic acid/stearic acid-mono/diglyceride, self-emulsifying properties of the shortenings intended for baking are achieved (superglycerolated shortenings).

The term "shortening" expressis verbis means to shorten something and is derived from baking properties. Due to the specific structure, monoglycerides are able to change the plasticizing action of starch and gluten in the preparation of dough by entering finely divided into the homogenous plasticized material, thus breaking up the materials and interrupting them to make the dough more smoother, i.e. shorter. At the same time the incorporation of air is facilitated so that, altogether, bakery products are obtained with increased volume and improved "shortness".

The essential components of margarine are edible fats and oils, drinking water, emulsifiers. As emulsifiers, lecithin, the egg yolk and/or monoglycerides and diglycerides of edible fatty acids may be used. Furthermore, the margarine may contain aroma finishing additives, sour milk, buttermilk, skim milk, fermented milk, cooking salt, starch sirup, citric acid and/or other edible acids, vitamins as well as permissible certified preservatives and certified dyestuffs (usually carotine or carotine-containing oils). Emulsifiers are obligatory auxiliary products in the preparation of margarine, because they enable the formation of water in oil emulsions. The most common ones are monoglycerides and plant lecithin assisting each other in the emulsifying action. Used in practice are products having about 40 and about 90%, respectively, of monoglycerides of $C_{16}/C_{18}$ acids (palmitic acid, stearic acid, also in mixture with oleic acid) which, in addition, contain 60 and 10%, respectively, of diglycerides. Additions of up to 0.5 and 0.25%, respectively, corresponding to about 0.2% of monoglyceride, based on the fatty phase, are common. In the preparation of low-calorie margarine, higher proportions of emulsifier are usually necessary.

The monoglycerides and diglycerides are obtainable by esterification of glycerol with fatty acids. Another route is the transesterification of triglycerides with glycerol. Furthermore, an enzymatic cleavage of triglycerides has lately found acceptance in technology. All methods result in a blend of monoglycerides, diglycerides, and triglycerides. During the esterification, an equilibrium mixture of about 60% of monoglycerides, 35% of diglycerides, and 5% of triglycerides is finally generated. The mixture is separated by molecular distillation. A disproportionation occurs to a minor extent at high temperatures in the film evaporator so that the monoglycerides or diglycerides contain small amounts of the other two esters and minor amounts of free fatty acids.

Because of the disproportionation at the temperatures prevailing in the film evaporator, monoglycerides having contents of more than 95% may not be obtained by molecular distillation at ambient pressure in an economically feasible manner. However, there exists a great interest in monoglycerides possessing a purity of 99% and more.

This is surprisingly achieved by the process according to this invention by means of the extraction with a supercritical extractant consisting of a highly volatile hydrocarbon having 2 to 6 carbon atoms and e.g. carbon dioxide and/or $N_2O$.

It is known that monoglycerides may be removed from a mixture of monoglycerides, diglycerides, and triglycerides by means of dense carbon dioxide. However, pressures of more than 350 at. at temperatures of 40° C. are necessary for this. Furthermore, the loading of dense carbon dioxide even at pressures of 350 at is still so small (less than 1%) that an economical recovery of monoglycerides of high purity is not possible.

Also suggested was the use of, for example, acetone as entrainer (DE-OS 2,340,566.5). By this the monoglycerides arrive at the head product during the countercurrent extraction as they are the more soluble components. However, the separation factors are relatively low, so that the recovery of pure monoglycerides is economically not interesting, all the more so, as the achieved loadings of 1 to 1.5% are small. Furthermore, the removal of the entrainer acetone from the product is cumbersome.

SUMMARY OF THE INVENTION

1. Purposes of the Invention

It is an object of the invention to provide a process for an economical recovery of monoglycerides and diglycerides.

It is a further object of the invention to provide an economical process for the recovery of monoglycerides of high purity.

These and other objects and advantages of the present invention will become evident from the description which follows.

2. Brief Description of the Invention

The present invention for a process for the recovery of monoglycerides and diglycerides from a mixture containing monoglycerides, diglycerides and triglycerides includes the following steps: A mixture containing monoglycerides, diglycerides, and triglycerides is extracted in a countercurrent system with a supercritical extractant, where the supercritical extractant contains as cosolvent a hydrocarbon in an amount of 30 to 90 weight-percent. The extractant is maintained in a supercritical state during the extraction process.

A hydrocarbon in an amount of from about 40 to 80 weight-percent can be employed as a cosolvent.

The supercritical extractant can be furnished by a member selected from the group consisting of carbon dioxide, nitrogen monoxide $N_2O$, sulfurhexafluoride, trifluoromethane, tetrafluoromethane, and mixtures thereof.

Hydrocarbons employed can contain from about 2 to 6 carbon atoms.

Carbon dioxide $CO_2$ can be used as an extractant and propane or butane can be used as cosolvent.

The extraction can be performed at a temperature in the range of from about 10° to 150° C. and preferably in the range of from about 20° to 80° C.

The extraction can be performed at pressures of from about 60 to 200 at., and preferably of from about 80 to 150 at.

The monoglycerides can be separated in the separation column for withdrawing the monoglycerides as a bottom product. An extract comprising diglycerides and triglycerides can be separated into diglycerides and triglycerides by fractionated pressure decrease and change of temperature in two regeneration columns.

A portion of the product, obtained in the first regeneration column, can be fed as reflux to the head of the separation column for an improved separation. A portion of the product, obtained in the second regeneration column, can be fed as reflux to the head of the first regeneration column.

The novel features which are considered as characteristic for the invention are set forth in the appended claims. The invention itself, however, both as to its method of operation, its products and physical requirements, together with additional objects and advantages thereof, will be best understood from the following description of specific embodiments and examples.

DESCRIPTION OF INVENTION AND PREFERRED EMBODIMENT

In accordance with the present invention, there is provided a process for the recovery of monoglycerides and diglycerides from a mixture containing monoglycerides, diglycerides and triglycerides by extraction in countercurrent direction with a supercritical extractant. The supercritical extractant contains as cosolvent a hydrocarbon in an amount of 30 to 90 weight-percent. The extractant remains in the supercritical state during the cyclic process.

Carbon dioxide $N_2O$, sulfurhexafluoride, trifluoromethane, tetrafluoromethane, or their mixture can be used as supercritical extractant.

Hydrocarbons having 2 to 6 carbon atoms, or their mixtures can be used as cosolvent.

Carbon dioxide $CO_2$ can be used as extractant, and propane or butane can be used as cosolvent.

A hydrocarbon in an amount of 40 to 60 weight-percent can be employed as a cosolvent. The extraction can be carried out in a temperature range of from 10° to 150° C., and preferably of from 20° to 80° C., and at pressures of from 60 to 200 at., and preferably of from 80 to 150 at.

After the separation of the monoglycerides as bottom product in the separation column, the extract consisting of diglycerides and triglycerides can be separated into diglycerides and triglycerides by fractionated pressure decrease and change of temperature in two consecutive regeneration columns.

For an improved separation, a portion of the product obtained in the first separator, can be fed as reflux to the head of the separation column, and a portion of the product, obtained in the second regeneration column, can be fed as reflux to the head of the first regeneration column.

The present invention discloses a process for the recovery of monoglycerides and diglycerides from a mixture containing monoglycerides, diglycerides, and triglycerides by extraction in countercurrent by a supercritical extractant, which process is characterized in that a supercritical extractant contains a hydrocarbon in an amount of 30 to 90 weight-percent, preferably 40 to 80 weight-percent, as a cosolvent, and wherein the extractant remains in the supercritical stage during the cyclical process.

Contrary to the process described in DE-OS 2,340,566.5, in the process of this invention, the monoglycerides do not pass to form a head product but they appear as bottom product of a separation column. The extractant at the head of the column contains the diglycerides and triglycerides as extracted material which may subsequently be separated from the extractant by fractionated separation. Two regeneration columns may be used for the fractionated separation. If there is no fractionated separation of the diglycerides and triglycerides, one regeneration column is sufficient.

By using for example carbon dioxide and/or $N_2O$ as supercritical extraction medium and by using low molecular hydrocarbons, such as ethane, propane, butane, as cosolvents, high separation factors may be achieved according to the process of the invention together with a high loading of the extractant. In this context, substances are termed to be in the supercritical state, the temperature of which at the respective pressures is higher than the critical temperature and, respectively, the pressure of which at the respective temperature is higher than the critical pressure. This pressure and temperature region corresponds to the hatched area of FIG. 1),, i.e. the area wherein at least either the pressure is higher than the critical pressure or the temperature is higher than the critical temperature in the phase diagram outside of the solid state area. While only insignificant effects have been observed when adding 10 weight-percent of the cosolvent, the separation factors surprisingly passes over a maximum value in the concentration range of 30 to 90 weight-percent of the cosolvent. In this range, the concentration of glycerides of 2 to 12 weight-percent, obtainable in the extractant, is so high that an economical operation is possible. A loading of the extractant of 6 weight-percent at 40° C. is obtained even at the low pressures of 120 at. With pure hydrocarbons, the separation factors are again very low, i.e. almost 1.

The extractant, for example consisting of $CO_2$ and the cosolvent, for example, propane, flows from bottom to top in the separation column. The mixture to be separated is fed about in the middle or at the head of the separation column, and the liquid phase flows downward in a countercurrent. On the way down, the latter becomes depleted of diglycerides and triglycerides until, finally, a bottom product, having a monoglyceride content of more than 99%, is obtained. The extractant, which leaves the head of said column, contains, apart from a minor residue of monoglycerides, the portions of diglycerides and triglycerides present in the feed. By a stepwise pressure decrease in two consecutive regeneration columns, the diglycerides may be preferably removed in the first regeneration column and, in the second regeneration column, the triglycerides may preferably be separated from the recycled extractant. A portion of the glycerides separated in the first regeneration column is introduced into the separation column as reflux, and the remainder is withdrawn as product. The glycerides which are optionally separated in the second regeneration column are partially returned to the head of the first regeneration column as reflux, and the remainder is withdrawn as further product which essentially contains only triglycerides. The product withdrawn from the first regeneration column contains the diglycerides. According to the process of this invention it is thus possible to separate in one operational step the mixture of monoglycerides, diglycerides, and triglycerides into three fractions which contain the monoglycerides, the diglycerides, and the triglycerides, respectively, in high purity.

Figure 2:
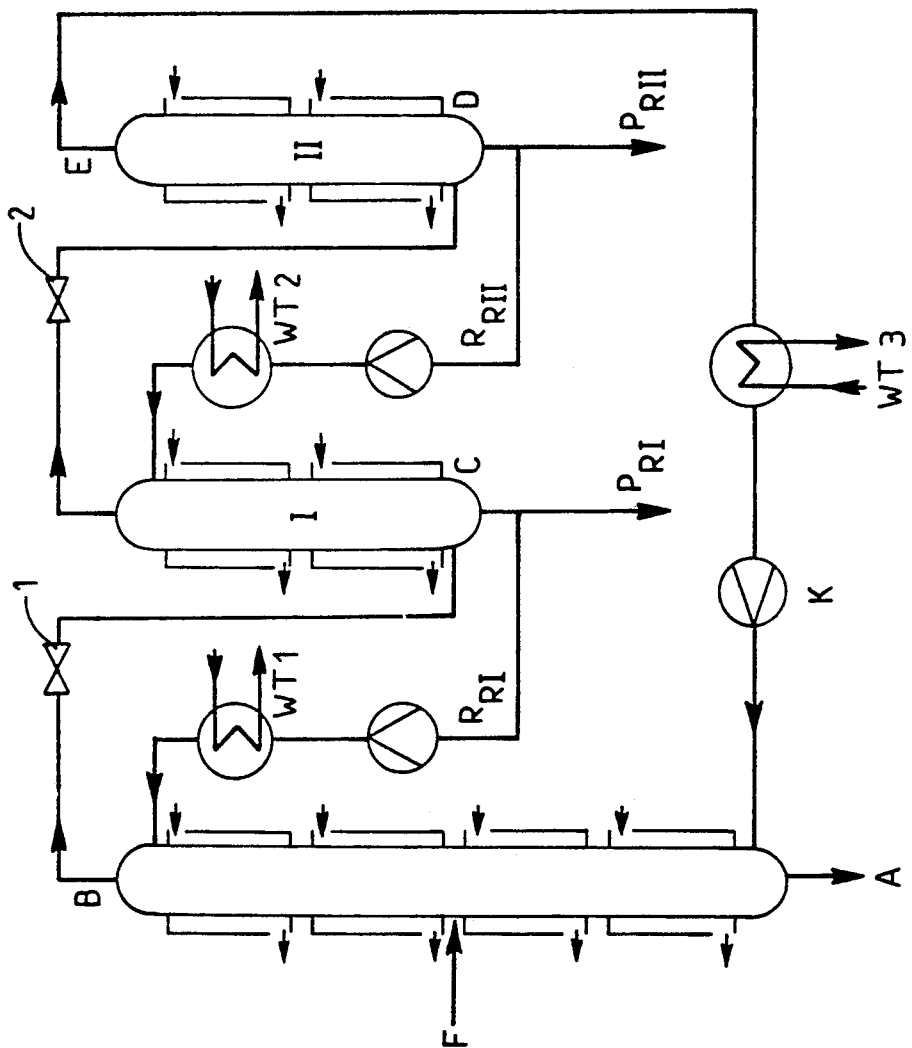

With the help of the schematic illustration in FIG. 2, an embodiment of the process of the present invention is shown in detail: The device consists of three columns of which one, i.e. the separation column, serves to separate the monoglycerides from a glyceride mixture. The monoglycerides are obtained as bottom product (point A). The regeneration columns I and II serve to remove the extracted components from the cycle gas.

The glyceride mixture is introduced into the separation column at the intermediate part (point F). The circulating extractant is preferably loaded with diglycerides and triglycerides in the separation column. At the same time, the extractant dissolves in the liquid phase which gets enriched in monoglycerides and flows downward.

The extractant loaded with the more soluble components diglycerides and triglycerides leaves the rectyfying section of separation column at the head (point B). The loaded extractant is pressure-released via a pressure-reducing valve 1 to arrive at the regeneration column I. Pressure and temperature in regeneration column I are chosen so that preferably diglycerides and the small remainder of monoglycerides are separated. The condensed phase is withdrawn from bottom (C) of regeneration column I and divided into product $P_{RI}$ and reflux $R_{RI}$. The recycled stream is introduced at the head of separation column after having passed the heat exchanger WT1. The extractant stream, loaded with triglycerides from regeneration column I, is pressure-released via the pressure-reducing valve 2 to arrive at the regeneration column II. In the regeneration column II, pressure and temperature are chosen so that the extractant leaving the column is free of low volatile components. The condensed phase is withdrawn from the bottom (D) of regeneration column II and divided into product $P_{RII}$ and reflux $R_{RII}$. After having passed the heat exchanger WT2, the reflux from regeneration column II is introduced at the head of regeneration column I. The recycle system enables the fractionation of diglycerides and triglycerides. From regeneration column I, a diglyceride-rich bottom product is obtained, while from regeneration column II, a triglyceride-rich bottom product is withdrawn.

The resulting bottom products are continuously withdrawn and pressure-released and collected in containers. The amounts of gaseous solvents escaping from the solution are returned into the cycle via a compressor K. The regenerated cycle gas, having left the regeneration column I at point E and having passed the heat exchanger WT3, is again fed into separation column by means of a compressor K.

In the fractionated separation of components dissolved in the extractant when operating isothermally, the pressure in the first regeneration column is decreased by about 10 to 60 bar, preferably 20 to 50 bar, compared to the pressure in the separation column.

The fractioned separation in the first regeneration column, however, can also be achieved by isobar operation. In this case, the temperature in the regeneration column is increased by 10° to 80° C., preferably by 20° to 50° C., compared to the temperature in the separation column. A combination of pressure decrease and temperature increase is also possible.

The conditions of separation in the second regeneration column correspond to the conditions of the regeneration of the extractant without any fractionation. The regeneration of the extractant is effected either by pressure release alone or by pressure release together with simultaneous temperature increase. The pressure during the regeneration is 30 to 80 bar in a temperature range of 40° to 120° C.

EXAMPLE 1

A glyceride mixture consisting of 60.9 weight-percent of monoglycerides, 35.3 weight-percent of diglycerides, 3.4 weight-percent of triglycerides of oleic acid and 0.4 weight-percent of free acids was pumped into the middle of a separation column at a temperature of 40° C. and a pressure of 120 bar and subjected to extraction. As extractant a mixture of 42 weight-percent of carbon dioxide and 58 weight-percent of propane was used, which mixture is supercritical under the operation conditions, i.e. exists and forms in one single phase. The extractant was loaded with 3.1 weight-percent of glycerides. The column was 4 m high and contained a Sulzer wire-net packing CY. The extractant stream leaving the head of the separation column was transferred into the regeneration column I. The operational conditions in the regeneration column I were 60.5 bar and 104° C. By simultaneous heating to 104° C. and pressure decrease to 60.5 bar, the loading of the extractant decreased to 0.08 weight-percent. The thus regenerated extractant was cooled to 40° C. and returned to the bottom of the separation column by means of a cycle compressor. A portion of the product separated in the regeneration column I was fed to the head of the separation column as reflux. The obtained bottom product contained 98.4 weight-percent of monoglycerides, 1.3 weight-percent of diglycerides and 0.3 weight-percent of free fatty acids. The concentration of triglycerides was below the detection limit of 0.005 weight-percent. The head product obtained in the regeneration column I contained 31.4 weight-percent of mono-glycerides, 59.8 weight-percent of diglycerides, 8.9 weight-percent of triglycerides and 0.4 weight-percent of free fatty acids. There was used only one regeneration column, because there was no fractionated separation of diglycerides and triglycerides.

EXAMPLE 2

The same starting product as in example 1 was employed and extracted in a separation column at 20° C. and 120 bar by the same extractant as in example 1. The separation column, however, was only 2 m high. The regeneration of the extractant was effected at 98° C. and 57 bar. The loading of the extractant in the separation column was 3 weight-percent. With the high solvent ratio of 30, the following products were obtained: bottom product consisting of 99.5 weight-percent of monoglycerides, 0.3 weight-percent of diglycerides and 0.2 weight-percent of free fatty acids; head product consisting of 39.1 weight-percent of monoglycerides, 52.1 weight-percent of diglycerides, 8.4 weight-percent of triglycerides and 0.4 weight-percent of free fatty acids.

EXAMPLE 3

A glyceride mixture consisting of 53 weight-percent of monoglycerides, 31 weight-percent of diglycerides, and 13 weight-percent of triglycerides of stearic acid, and 3 weight-percent of free fatty acids was fed to the middle of a separation column at 140 bar and 50° C. A portion of the product separated in the regeneration column I was fed to the head of the separation column as reflux. A mixture of 70 weight-percent of propane and 30 weight-percent of carbon dioxide was used as extractant. The stearic acid glyceride mixture, which is present as a solid under normal conditions, is liquid under the mentioned operational conditions, the extractant mixture is supercritical, i.e. there is one phase. The height of the column was 8 m. Sulzer packings, type CY, were used. The regeneration was effected at 105° C. and 55 bar. The loading of the extractant with glycerides was 4 weight-percent in the separation column. With a solvent ratio of 30, the following products were obtained: bottom product consisting of 99.0 weight-percent of monoglycerides, 0.4 weight-percent of diglycerides, and 0.6 weight-percent of free fatty acids; head product consisting of about 5 weight-percent of monoglycerides, 70 weight-percent of diglycerides, 20 weight-percent of triglycerides and 5 weight-percent of free fatty acids.

EXAMPLE 4

A glyceride mixture of 57.5 weight-percent of monoglycerides, 36 weight-percent of diglycerides, 6.15 weight-percent of triglycerides, and 0.35 weight-percent of free fatty acids, the glycerol esters being mainly derived from fatty acids with 18 carbon atoms (content of $C_{14}$ acids 4% of $C_{16}$ acids 8%), was introduced into the middle of a separation column at 120 bar and 40° C. As extractant, a mixture of 57 weight-percent of propane and 43 weight-percent of carbon dioxide was used. The column was 16 m high; Sulzer packings, type CY, were also used. The extractant, with a head loading of difficultly volatile or low volatile components of about 10 weight-percent was partially pressure-released to 80 bar at 40° C. in the first regeneration column. By this, the diglycerides and the minor remainder of monoglycerides were separated from the solution with preference, while the triglycerides remained dissolved. The extractant, which was loaded mainly with triglycerides, was subjected to a further pressure release to 50 bar in a second regeneration column, the temperature being raised to 120° C. At these conditions, the extractant loses its solvent capacity for difficultly volatile products almost completely. As bottom product a triglyceride-rich mixture was obtained. The regenerated extractant was again fed to the bottom of the separation column. To increase the diglyceride concentration in the bottom of the first regeneration column and to minimize losses of monoglyceride, a portion of the condensate from the first regeneration column was fed to the head of the separation column as reflux. In analogous manner, a portion of the condensate from the second regeneration column, was fed to the head of the first regeneration column as reflux in order to increase the diglyceride concentration in the bottom of the first regeneration column. With a solvent ratio of about 30, the following products were obtained: Separation column: Bottom product consisting of 99.2 weight-percent of monoglyceride, 0.4 weight-percent of diglyceride, and 0.4 weight-percent of free fatty acids. First regeneration column: Bottom product consisting of 95 weight-percent of diglyceride, 1 weight-percent of monoglyceride, 3.7 weight-percent of triglyceride, and 0.3 weight-percent of free fatty acids. Second regeneration column: Bottom product consisting of about 90 weight-percent of triglyceride, g weight-percent of diglyceride, 0.8 weight-percent of monoglyceride, and 0.2 weight-percent of free fatty acids.

It will be understood that each of the steps, conditions and reagents described above, or two or more together, may also find a useful application in other types of reactions, recovery procedures and products differing from the types described above.

While the invention has been illustrated and described as embodied in the context of a process for the recovery of monoglycerides and diglycerides from a mixture containing monoglycerides, diglycerides, and triglycerides, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A process for the recovery of monoglycerides and diglycerides from a mixture containing monoglycerides, diglycerides, triglycerides, and obtained by esterification of glycerol with fatty acids, transesterification of triglycerides with glycerol, or enzymatic cleavage of triglycerides, comprising extracting a mixture containing monoglycerides, diglycerides, and triglycerides in a countercurrent system with a supercritical extractant, wherein the supercritical extractant containing a hydrocarbon in an amount of 30 to 90 weight-percent and wherein the hydrocarbon acts as a cosolvent; and maintaining the extractant in a supercritical state during the extraction process;

wherein the supercritical extractant is furnished by a member selected from the group consisting of carbon dioxide, nitrogen monoxide $N_2O$, sulfurhexafluoride, trifluoromethane, tetrafluoromethane, and mixtures thereof;

wherein hydrocarbons employed contain from about 2 to 6 carbon atoms.

2. The process according to claim 1 wherein the hydrocarbon is employed in an amount of from about 40 to 80 weight-percent as a cosolvent.

3. The process according to claim 1 wherein carbon dioxide $CO_2$ is used as an extractant and wherein propane is used as cosolvent.

4. The process according to claim 1 wherein carbon dioxide $CO_2$ is used as extractant and wherein butane is used as cosolvent.

5. The process according to claim 1 wherein the extraction is performed at a temperature in the range of from about 10° to 150° C.

6. The process according to claim 5 wherein the extraction is performed at a temperature in the range of from about 20° to 80° C.

7. The process according to claim 5 wherein the extraction is performed at pressures of from about 60 to 200 at.

8. The process according to claim 5 wherein the extraction is performed at pressures of from about 80 to 150 at.

9. The process according to claim 1 further comprising separating the monoglycerides in the separation column for withdrawing the monoglycerides as a bottom product; and separating an extract comprising diglycerides and triglycerides into diglycerides and triglycerides by fractionated pressure decrease and change of temperature in two consecutive regeneration columns.

10. The process according to claim 1 further comprising
feeding a portion of the product, obtained in the first regeneration column, as reflux to the head of the separation column for an improved separation; and
feeding a portion of the product, obtained in the second regeneration column, as reflux to the head of the first regeneration column.

11. A process for the recovery of monoglycerides and diglycerides from a mixture containing monoglycerides, diglycerides and triglycerides by extraction in countercurrent direction with a supercritical extractant, wherein the supercritical extractant contains as cosolvent a hydrocarbon in an amount of 30 to 90 weight-percent and wherein the extractant remains in the supercritical state during the cyclic process.

12. The process according to claim 11, wherein carbon dioxide, nitrogen monoxide $N_2O$, sulfurhexafluoride, trifluoromethane, tetrafluoromethane, or their mixture are used as supercritical extractant.

13. The process according to claims 11, wherein hydrocarbons having 2 to 6 carbon atoms, or their mixtures are used as cosolvent.

14. The process according to claims 11, wherein carbon dioxide $CO_2$ is used as extractant, and propane is used as cosolvent.

15. The process according to claim 11, wherein carbon dioxide $CO_2$ is used as extractant, and butane is used as cosolvent.

16. The process according to claims 11, wherein a hydrocarbon in an amount of 40 to 80 weight-percent is employed as a cosolvent,
wherein the extraction is carried out in a temperature range of from 10° to 150° C., and
wherein the extraction is carried out at pressures of from 60 to 200 at.

17. The process according to claim 16, wherein the extraction is carried out at pressures of from 80 to 150 at and at temperatures of from 20° to 80° C.

18. The process according to claim 11, wherein, after the separation of the monoglycerides as bottom product in the separation column, the extract consisting of diglycerides and triglycerides is separated into diglycerides and triglycerides by fractionated pressure decrease and change of temperature in two consecutive regeneration columns.

19. The process according to claim 18, wherein, for an improved separation, a portion of the product obtained in the first regeneration column is fed as reflux to the head of the separation column, and a portion of the product, obtained in the second regeneration column, is fed as reflux to the head of the first regeneration column.

20. A process for the recovery of monoglycerides and diglycerides from a mixture containing monoglycerides, diglycerides, triglycerides, and obtained by esterification of glycerol with fatty acids, transesterification of triglycerides with glycerol, or enzymatic cleavage of triglycerides, and mixture thereof, comprising
extracting a mixture containing monoglycerides, diglycerides, and triglycerides in a countercurrent system with a supercritical extractant, wherein the supercritical extractant containing a hydrocarbon in an amount of 40 to 80 weight-percent and wherein the hydrocarbon acts as a cosolvent; and
maintaining the extractant in a supercritical state during the extraction process;
wherein the supercritical extractant is furnished by a member selected from the group consisting of carbon dioxide, nitrogen monoxide $N_2O$, sulfurhexafluoride, trifluoromethane, tetrafluoromethane, and mixtures thereof;
wherein hydrocarbons employed contain from about 2 to 6 carbon atoms.

21. A process for the recovery of monoglycerides and diglycerides from a mixture containing monoglycerides, diglycerides, and triglycerides, and obtained by esterification of glycerol with fatty acids, transesterification of triglycerides with glycerol, or enzymatic cleavage of triglycerides, comprising extracting a mixture containing monoglycerides, diglycerides, and triglycerides in a countercurrent system with a supercritical extractant, wherein the supercritical extractant containing a hydrocarbon in an amount of 30 to 90 weight-percent and wherein the hydrocarbon acts as a cosolvent; and
maintaining the extractant in a supercritical state during the extraction process;
wherein the extraction is performed at a temperature in the range of from about 10° to 150° C.; wherein the extraction is performed at pressures of from about 60 to 200 at.

22. The process according to claim 21 wherein
the hydrocarbons employed contain from about 2 to 6 carbon atoms.

23. A process for the recovery of monoglycerides and diglycerides from a mixture containing monoglycerides, diglycerides, and triglycerides, and obtained by esterification of glycerol with fatty acids, transesterification of triglycerides with glycerol or enzymatic cleavage of triglycerides, comprising extracting a mixture containing monoglycerides, diglycerides, and triglycerides in a countercurrent system with a supercritical extractant, wherein the supercritical extractant containing a hydrocarbon in an amount of 30 to 90 weight-percent and wherein the hydrocarbon acts as a cosolvent; and maintaining the extractant in a supercritical state during the extraction process;

wherein the supercritical extractant is furnished by a member selected from the group consisting of carbon dioxide, nitrogen monoxide $N_2O$, sulfurhexafluoride, trifluoromethane, tetrafluoromethane, and mixtures thereof;

wherein hydrocarbons employed contain from about 2 to 6 carbon atoms;

wherein the extraction is performed at a temperature in the range of from about 10° to 150° C.;

wherein the extraction is performed at pressures of from about 60 to 200 at.

* * * * *